US009372164B2

(12) United States Patent
Cancre et al.

(10) Patent No.: US 9,372,164 B2
(45) Date of Patent: Jun. 21, 2016

(54) XRF INSTRUMENT WITH REMOVABLY ATTACHED WINDOW PROTECTING FILMS

(71) Applicants: Fabrice Cancre, Lexington, MA (US); Ted Michael Shields, Waltham, MA (US); Jiawei Tan, Bedford, MA (US)

(72) Inventors: Fabrice Cancre, Lexington, MA (US); Ted Michael Shields, Waltham, MA (US); Jiawei Tan, Bedford, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 132 days.

(21) Appl. No.: 14/249,857

(22) Filed: Apr. 10, 2014

(65) Prior Publication Data

US 2014/0307849 A1 Oct. 16, 2014

Related U.S. Application Data

(60) Provisional application No. 61/810,424, filed on Apr. 10, 2013.

(51) Int. Cl.
*G01N 23/223* (2006.01)

(52) U.S. Cl.
CPC ........ *G01N 23/223* (2013.01); *G01N 2223/301* (2013.01); *G01N 2223/317* (2013.01); *G01N 2223/318* (2013.01)

(58) Field of Classification Search
CPC . G01N 23/223; G01N 2223/076; G21K 1/06; A61B 6/485; A61B 6/10; A61B 6/102; A61B 6/107; A61B 6/582; A61B 6/585; H01J 5/18; H01J 35/18; G03F 7/70808
USPC ............................. 378/44, 45, 161, 204, 207
See application file for complete search history.

(56) References Cited

U.S. PATENT DOCUMENTS 7,474,730 B2 * 1/2009 Puusaari .............. G01N 23/223
378/161
2013/0279654 A1 * 10/2013 Kantonen ........... G01N 23/223
378/49

* cited by examiner

*Primary Examiner* — Jurie Yun
(74) *Attorney, Agent, or Firm* — C. Tricia Liu

(57) ABSTRACT

Herein disclosed is an x-ray florescence (XRF) test system which comprises an XRF test instrument used for testing a test target's responses to X-rays, the instrument including a test window allowing the X-ray and its responsive energy to pass through, and at least one window protecting film allowing X-rays to pass through and providing protections to the window, the film being configured to be coupled with the window in a fashion to be removed from or applied or reapplied over the window. The corresponding calibration mode can be manually or automatically applied according to the specific film presently in use.

18 Claims, 6 Drawing Sheets

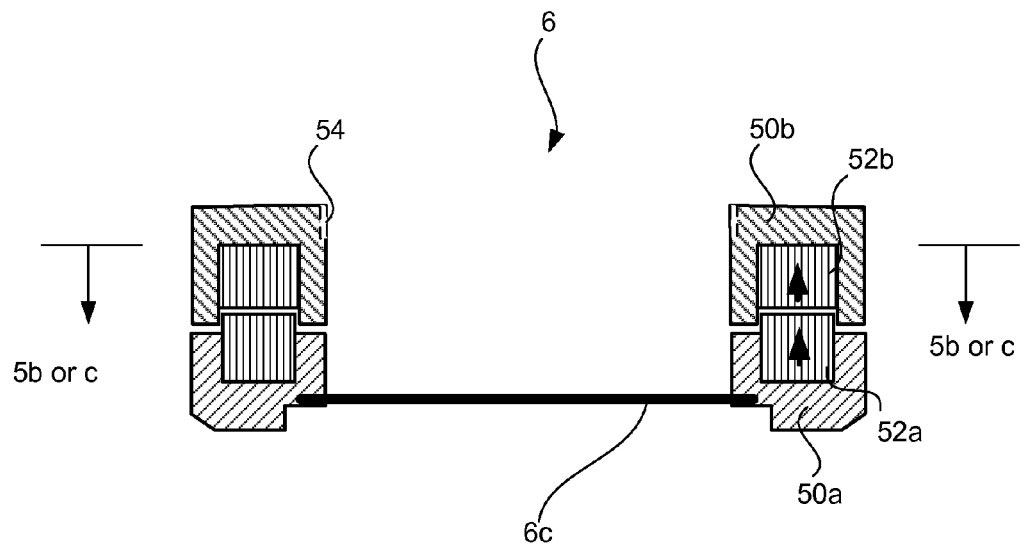
Fig. 5a
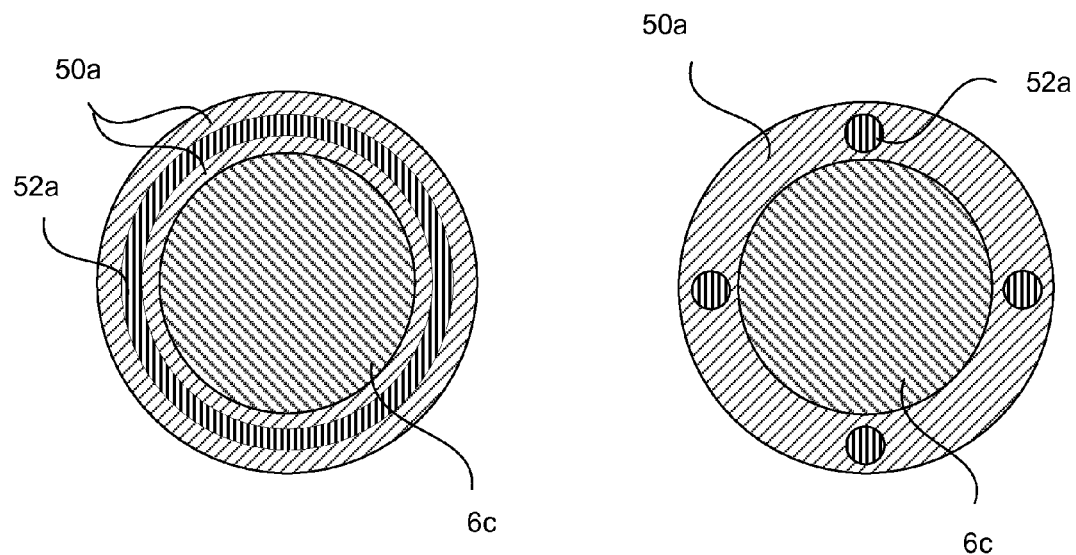
Fig. 5b
Fig. 5c

XRF INSTRUMENT WITH REMOVABLY ATTACHED WINDOW PROTECTING FILMS

RELATED APPLICATIONS

This application claims benefit of and priority to U.S. Provisional Application entitled "REMOVABLE WINDOW PROTECTING FILMS AND A METHOD OF APPLYING SUCH TO AN XRF/XRD DEVICE" with application No. 61/810,424 filed Apr. 10, 2013 under 35 U.S.C. §§119, 120, 363, 365, and 37 C.F.R. §1.55 and §1.78 incorporated herein by this reference.

BACKGROUND OF THE INVENTION

In X-ray fluorescence (XRF) testing, portable testing instruments are often subject to harsh environment. The instrument test windows often need to be protected from possible dusting, intrusion and abrasion from the test material.

However, applying protecting material to the test window often impedes the accuracy and sensitivity of the test result, particularly for testing elements with low atomic numbers.

For example, polyethylene or polyimide is often used material for window shields or a cover. Polyethylene is more transparent and therefore less of absorbing to low energy X-rays than polyimide, but is not as resistant to punctures.

It is therefore desirable to have the sensitivity that polyethylene yields for elements with lower atomic numbers, and with the same instrument to have the physical protection offered by thicker polyimide when the testing requirement for sensitivity is not as demanding, such as for testing Titanium (Ti) or other higher atomic numbers. It provides many benefits for an instrument to be equipped with a layer of window guard or protecting film that can be easily applied on or taken off for testing elements with higher or lower atomic numbers, respectively.

Various shields and/or window guards have been seen in existing practice designed for X-ray devices such as handheld X-ray fluorescence (XRF) instruments. Examples include U.S. Ser. No. 13/551,232; U.S. Pat. Nos. 7,430,274; 7,375,359; 7,375,358; 6,965,118; and 7,671,350, as well as WO 00/37928, are all incorporated herein by this reference. See also U.S. Published Application No. US-2008-0152079. However, none of these background arts have been seen to provide the simple, low cost and convenient solution as described herein in the present disclosure.

SUMMARY OF THE INVENTION

The fragile sealing window used in an X-ray analytical instrument can be protected from encounters with foreign objects by applying the protection film with embodiments of the present disclosure.

It is a general object of the present disclosure to overcome the problems associated with the background art by introducing an economical, simple, easy-to-apply and re-attachable window guard that engages whenever: a) a measurement mode is for testing heavier elements, b) a penetrating object is sensed to be in close proximity to the detector sealing window during a measurement mode, c) the instrument is not in usage, or d) determined by the operator to apply, etc.

The foregoing and other objects of the present disclosure may be realized with a replaceable protective film that covers the detector window, and can be removed and reapplied.

In accordance with various embodiments of the invention, the protective covering or guard film may be attached on top of the detector window by adhesive means, or taken off and re-attached to the window depending on the need of the operation of the instrument. Other means of attaching, removing and re-attaching can include using other coupling means, such as magnetic coupling, thread screw coupling, etc.

Other features and advantages of the present invention will become apparent from the following description of the invention which refers to the accompanying drawings.

BRIEF DESCRIPTION OF THE DRAWINGS

The drawings presented are not necessarily to scale. Emphasis is placed upon illustrating the principles of the preferred embodiment of the method.

FIGS. 5a, 5b and 5c exhibit another means of attaching and re-attaching the protective film by using magnets as couplings.

DETAILED DESCRIPTION OF THE PREFERRED EMBODIMENT

The method proposed by the preferred embodiment is herein presented by referring to FIGS. 1-5c.

Figure 1:
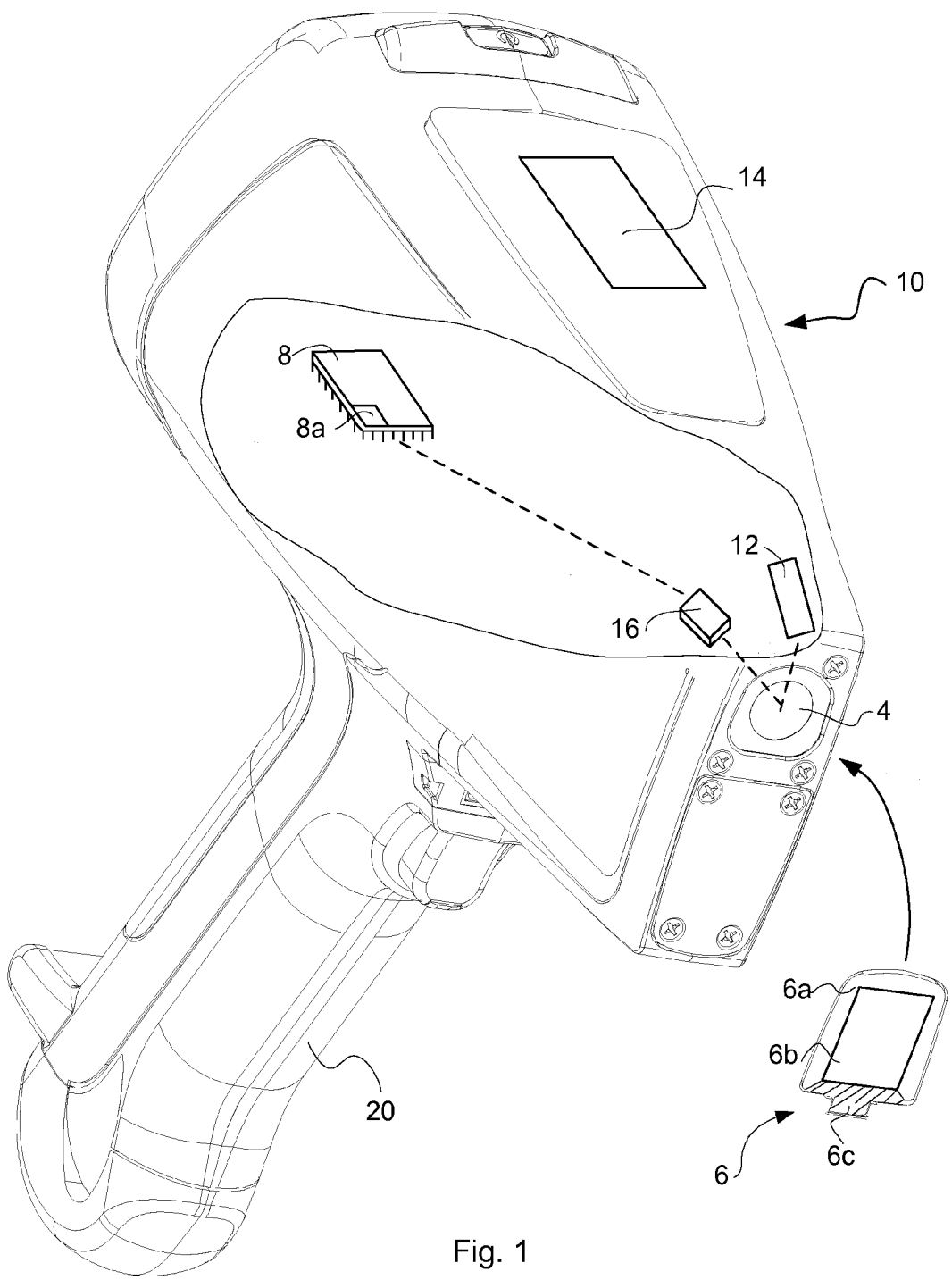
FIG. 1 is a schematic of an XRF instrument with a removable protective film ready to be applying over the window of the XRF instrument according to the present disclosure.

As seen in FIG. 1, a conceptual view of an XRF instrument 10 is configured to couple with a plurality of protection films 6, one at a time during operation. A test window 4 is devised as in conventional XRF instruments. An important novel aspect of the solution herein presented includes the employment of a plurality of removable protection films 6, with which any number can be applied over a test window 4 according to the present invention.

The XRF instrument further optionally includes an X-ray source 12, a detector 16, a data processor 8 and a display 14, largely in the same way as conventional XRF instruments.

An immediate exemplary usage of such embodiment is to affix the commonly used polyethylene film or coating to window 4 in a non-removable fashion as conventionally done in some XRF instruments. The sensitivity that polyethylene yields for elements with lower atomic numbers is desirable for testing samples with lower atomic numbers. Therefore, no additional removable film or guard 6 is needed for such situation. However, with the same instrument 10, in order to achieve the physical protection needed for many testing environments, thicker polyimide removable film 6, such as polyimide 75 μm, can be applied over the existing non-removable polyethylene film or coating. This is the most desirable when the testing requirement for sensitivity is not as demanding, such as testing for Titanium (Ti) or other higher atomic numbers.

Figure 2:
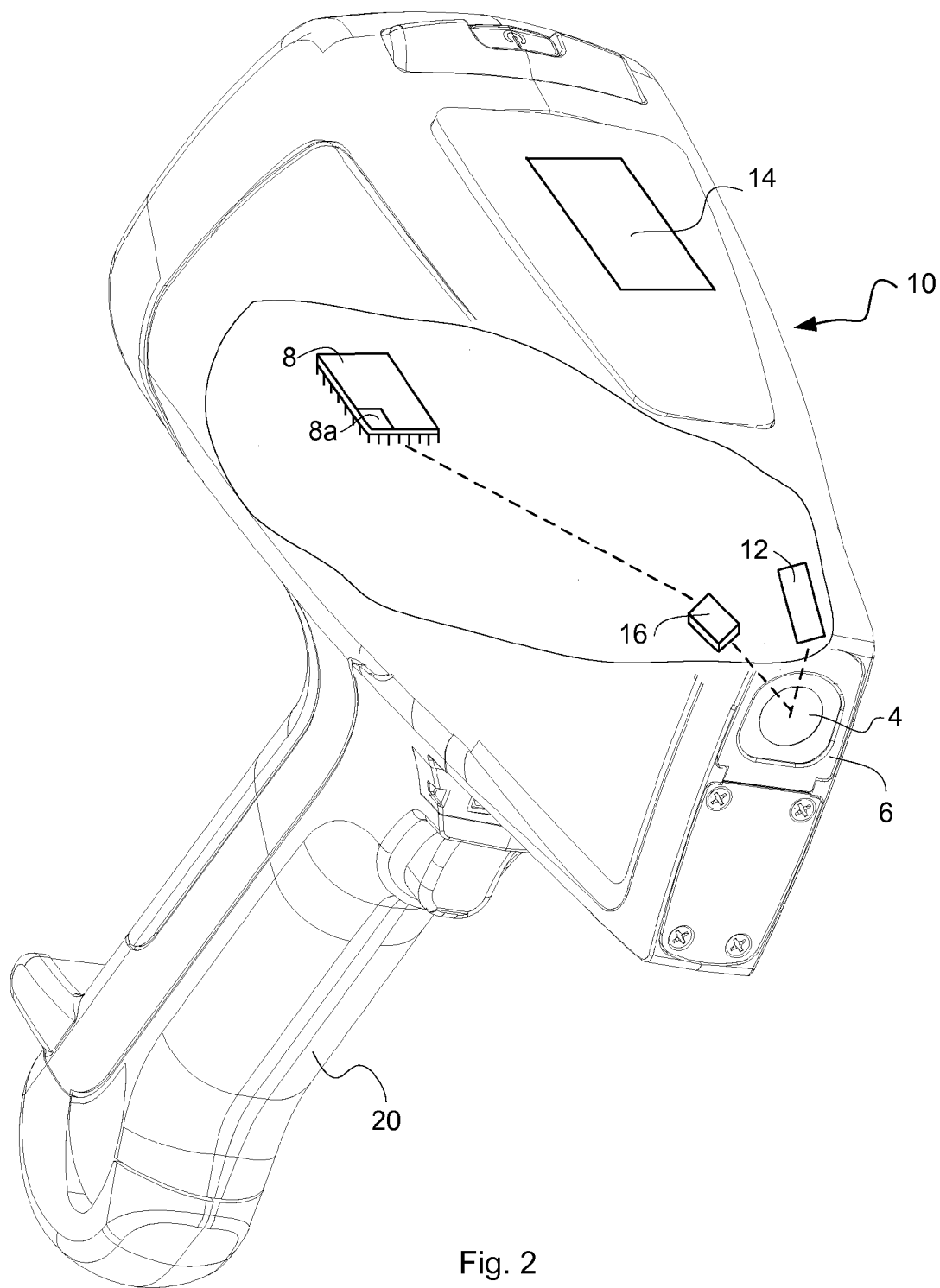
FIG. 2 is a schematic of the XRF instrument in FIG. 1 with the removable protective film applied over the window.

It should be appreciated that the usage of any number of, and any combination of any kinds of films, collectively numerated as 6 in FIGS. 1 and 2 should be determined by the testing specifics, and the usage of all such should be within the scope of the present disclosure.

For example, the fixed layer of film is optional, and it doesn't have to be polyethylene. Polyimide with 25 µm is another often used film that can be used as the fixed layer. The removable film 6 can be also many choices.

Reference is still made to FIG. 1. Removable film 6 is preferably attached over window 14 by using a removable attaching means. Accordingly, film 6 is shown to be configured to include an adhesive backing 6a encircling the edge of film 6. Alternatively, the adhesive backing 6a can be applied in sections, instead of continuously encircling the edge.

Continuing to refer to FIG. 1, film 6 can optionally have an extruded tab 6c allowing easy application onto and removal from window area 4. Preferably, working area 6b should be left clean from adhesives and human touch.

It should be appreciated that removable film 6, adhesive backing 6a, tab 6c and working area 6b each and all can take any shape to suit for specific XRF instruments, and any such shape used by a removable film falls within the scope of the present invention.

It should also be appreciated that the adhesive material (not shown) applied to backing 6a can be of any material suited for the purpose of attaching film 6 in a removable manner.

Referring to FIG. 2, XRF instrument 10 is conceptually shown when removable film 6 is applied onto window 4.

Figure 3:
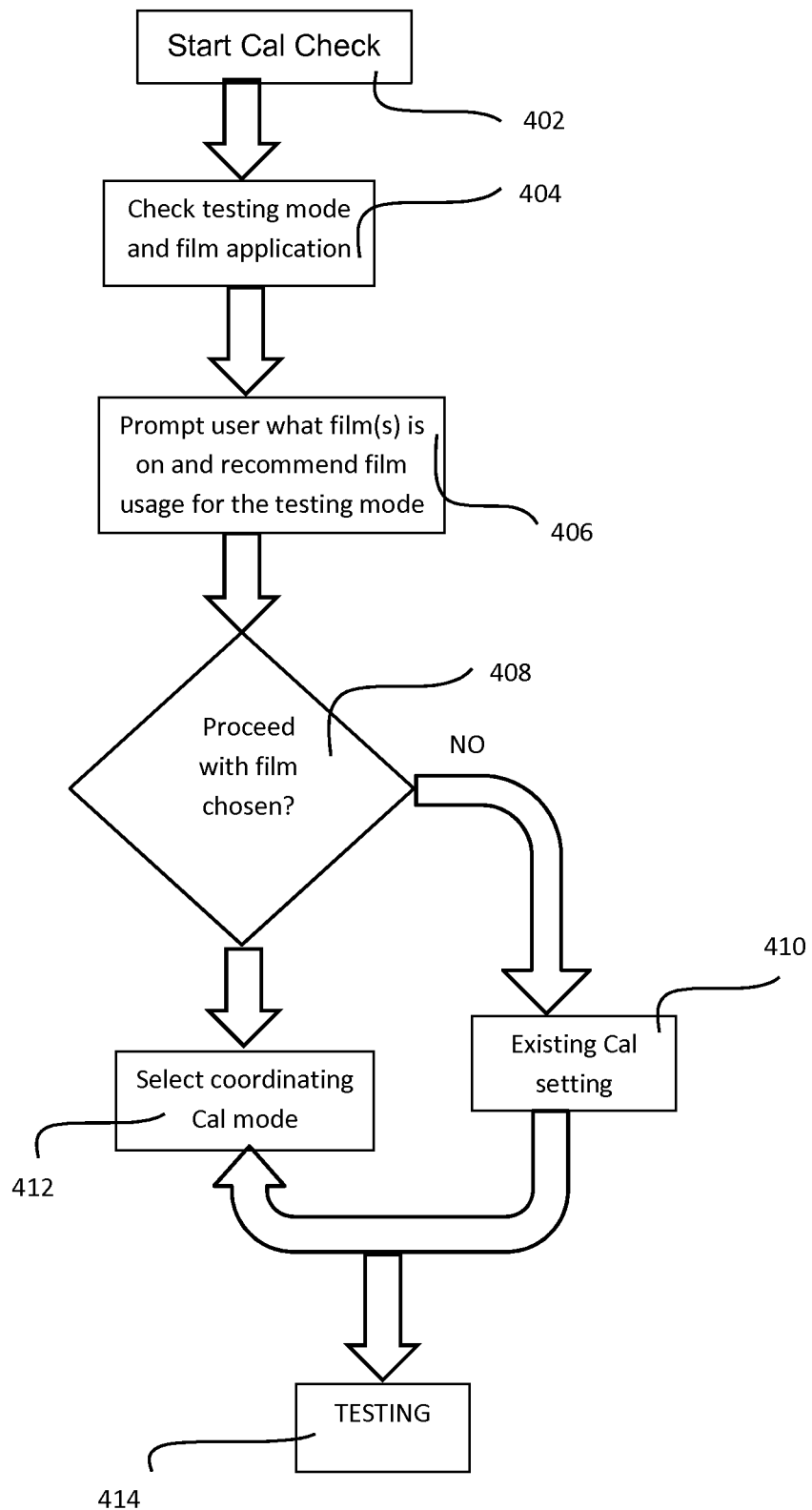
FIG. 3 is a flowchart of the process for operating the XRF instrument accommodating the application of the protective film.

Reference is now primarily made to FIG. 3 with continued reference to FIG. 1. FIG. 3 is a flowchart showing an operational procedure related to the usage of the embodiment shown in FIG. 1.

In order to accommodate the usage of a plurality of removable films according to the present invention, instrument 10 is preferably devised with a plurality of corresponding calibration modes, preloaded onto processor 8.

It should be noted that the different calibration modes for different types of removable films 6 can be either designed in a new XRF instrument, or achieved by modifying an existing calibration module or functional block residing on the processor of an existing XRF product. The modified calibration module is shown in FIG. 1 as 8a. It can also alternatively be calibrated in a field operation or in a manufacturing set up, all of which should be within the scope of the present invention.

The method of calibrating an XRF instrument for a specific window protection is commonly known. Different calibration modes can be achieved in manufacturing settings for different types of the protection films/guards.

Alternatively, if the quality and thickness of the protecting films are substantially homogenous and standard, one can populate the values of different calibration modes by calculating the energy-dependent effect on the spectrum caused by the corresponding film. One can conduct sufficient number of calibration runs for a specific protecting film, which yield a calibration factor for the film by comparing to the energy reading of the same instrument without the film applied on the same set of samples. With the standard calibration factors established, using the example film Kapton 25 for element Mo testing, one can use the calibration factor associated with this specific protecting film to calculate the new calibration value with the protection film/guard based on normally known calibration values without the protection film. The result specific to this calibration mode for Kapton 25 for Mo testing can be stored in a memory (not shown) of the instrument. The following table shows an exemplary result of such calculation of the calibration mode.

TABLE 1

Calculating Calibration Values for Mo Testing with Kapton 25 as Window Guard

|  | Fe Region | Cu Region | Mo Region |
|---|---|---|---|
| Normal Calibration values | 54.8815 | 85.9407 | 176244 |
| Calibration Factor for film Kapton 25 | 0.9119102 | 0.98551094 | 0.97156215 |
| Calculated Calibration Values with WG | 50.047 | 84.6955 | 171232 |

It can be understood by those skilled in the art that, wherein in Table 1, the content in the top row denotes to "energy regions" associated with known elements in a known sample. "Normal Calibration values" denote the x-ray counts per second from the standard sample without the window guard or the film. "Calculated Calibration Values with WG" denote the x-ray counts per second from the same standard sample, with the window guard or the film.

Yet another note on the calibration modes is that it is preferable to prepare all possible calibration modes with corresponding calibration values for all possible combinations of using, or without using, any and any number of protection films provided with the instrument.

Continuing with FIG. 3, the calibration procedure is preferably made in a form executable functional code, and as a module herein named "film calibration module" 8a shown in FIG. 1. The calibration procedure preferably includes steps as follows.

In step 402, the operator starts testing by starting a "Cal check" with a calibration mode mostly used for a previous session of testing. i.e., light element or heavy atomic element. "Cal check" is commonly referred in XRF as shooting a sample of known elemental composition;

In step 404, calibration module 8a checks the film application to determine whether film is applied, and optionally to determine automatically what kind of film is applied on window 4.

Alternatively, when the known kind of element for testing, such as Mo, is provided to the instrument, module 8a can be configured to determine if the detected film 6 is the right match for such testing.

It should be understood that alternative step 404 can be that the calibration module 8a only checks if film 6 is applied or not, and prompts the operator to check if film 6 is the intended kind of film to be attached.

It can be understood by those skilled in the art that after the Cal Check is initiated at step 402, the energy reading on a known sample can indicate if a protection film is applied. And by comparing the known calibration factors stored in the instrument, such as that listed in Table-1, optionally the calibration module 8a can yield what kind of film is presently attached to the window. Further alternatively, the calibration module 8a can also yield what kind of film is presently attached to the window by comparing the ratios of a couple of know spectrum to a predetermined threshold of such ratios.

In step 406, calibration module 8a mostly via display 14 prompts operator whether film is applied and what kind of film is applied on window 4, and suggests the operator whether to change or remove film or alternatively change the calibration mode.

In step 408, module 8a further checks what film or no film is chosen by the operator. If a specific film is chosen, the procedure moves onto step 412. If no film is chosen, the procedure moves onto step 410.

In step 412, a specific calibration mode suited for the chosen film is chosen by the calibration module, and executed to calibration instrument 10. Alternatively, the operator can also choose the calibration mode via display 14.

In step 410, if the operator determines not to use any protection film and remove the same, the existing calibration mode for window 4 without additional re-attachable protection film 6 is executed to calibrate instrument 10. In the exemplary case shown in Table-1, the row of values of "Normal Calibration Values" is used.

In step 412, instrument 10 is ready for testing.

Figure 4A:
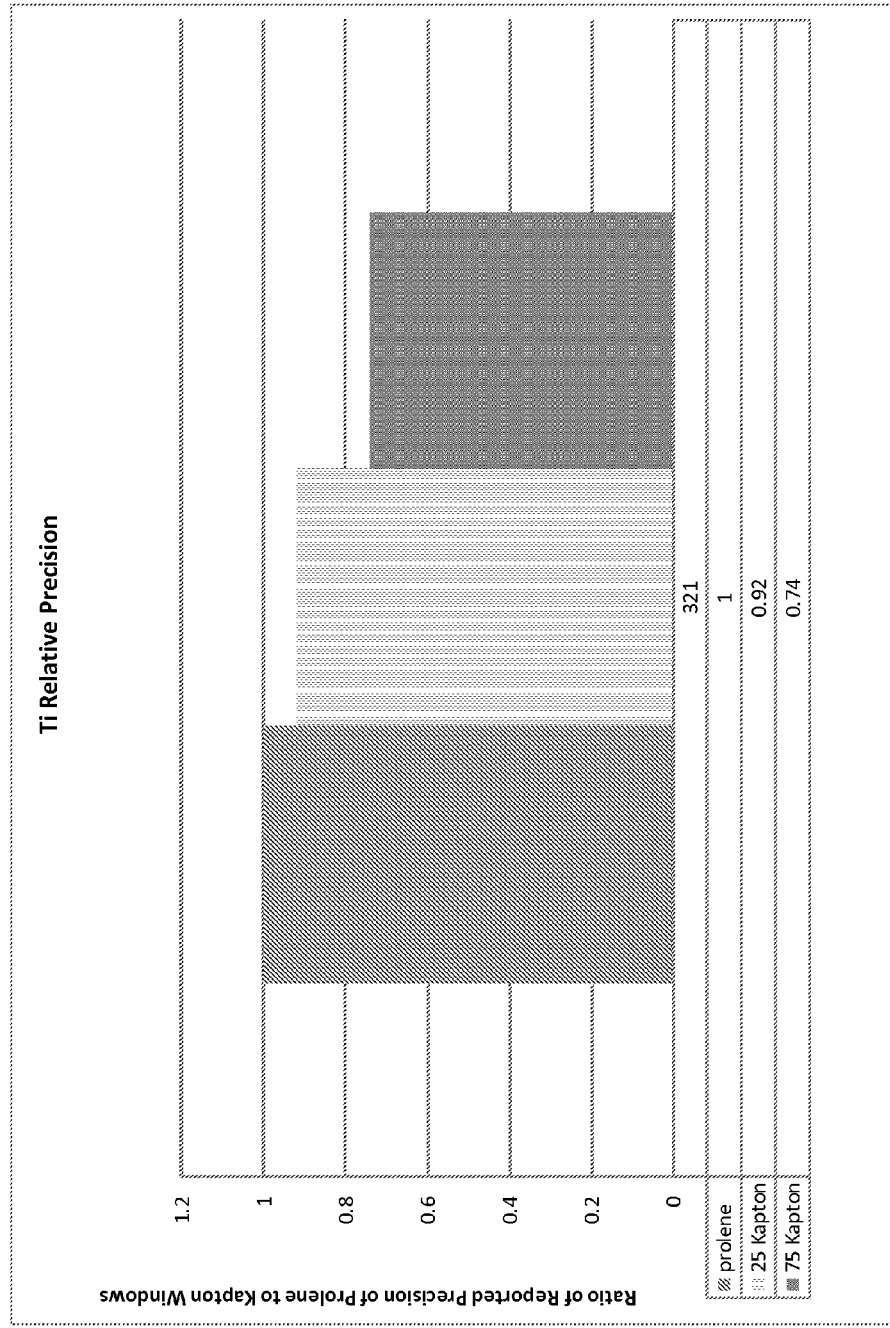
FIGS. 4a and 4b exhibit the effect of the protective films on different XRF measurements, made for light elements and heavy elements respectively.
Figure 4B:
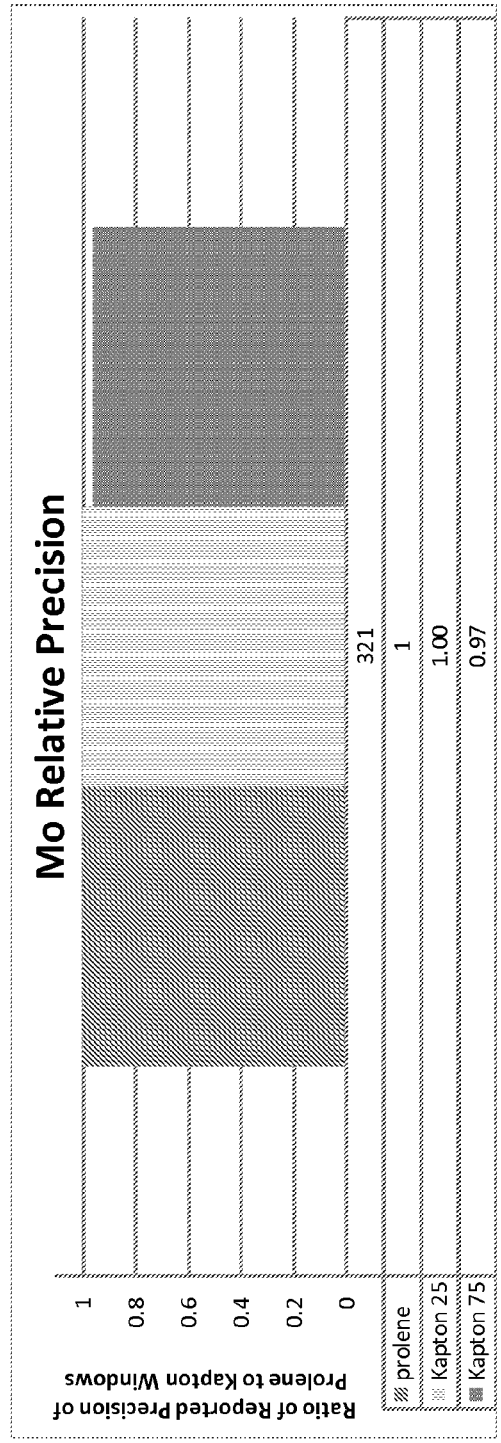

Reference is now made to FIGS. 4a and 4b, whereby two exhibitions are shown for the effect of adding removable films, presented as "ratio of precision of Prolene window", with Prolene (an example of a polyethylene window) exemplarily used as the fixed window base for cases. A Ti element of the lighter end of heavy atomic elements and a Mo element of the heavy atomic elements are used in FIGS. 4a and 4b, respectively. Both elements are tested within Alloy 321 for both cases. In addition, removable films Kapton 25 (an example of a polyimide window) and Kapton 75 are representatively used to compare their respective effectiveness against a fixed window with Prolene.

As can be seen in FIG. 4a that the lighter end of the heavier atomic elements (e.g. Ti) is affected the most by the effect of changing or adding removable films.

As can be seen in FIG. 4b that higher end of heavier atomic elements, such as Mo, is not as affected by adding removable films. Therefore, adding removable films for extra protection is desirable.

The comparison of FIGS. 4a and 4b indicates the benefit of versatility allowing adding or removing protection films to the text window of the XRF instruments.

Reference is now made to FIGS. 5a, 5b and 5c, which exhibit an alternative means of attaching and re-attaching the protection film 6. In this alternative attaching method, magnetic attraction force is used to stick or attach the film onto the window of the XRF instrument.

As seen in FIGS. 5a, 5b and 5c, the re-attachable film 6 with magnetic coupling comprises protection film main body 6c, a first holder 50a holding film 6c and one set of magnets 52a, a second holder 50b holding a second set of magnets 52b. As shown in FIG. 5a, it can be appreciated that holder 50b is placed along a window perephery immediately outside and surrounding the window and corresponding matching magnetic coupling 52a in positions. It should be noted that elements 52a and 50b can each be any of the permanent magnets or ferromagnetic material as long as 52a and 52b forms a magnet coupling strong enough to hold the film onto the window. Magnetic couplings 52a and 52b can also be in the forms of whole piece, such as shown in FIG. 5b, or of discrete discs, such as shown in FIG. 5c, that are configured to exert magnetic force on its corresponding counter-parts.

There can be optional attaching means such as a screw thread 54 for the second holder 50b to be attached to window 4, with the corresponding coupling thread on window 4 (not shown). It should be understood by those skilled in the art that other attaching means can be used instead to thread the attached to the second holder 50b to the window.

It can be understood that this alternative magnetic coupling provides a similar advantage as that of adhesive coupling, and that it is simple and convenient for the operator to attach and re-attach the protection film onto or from the window.

It should be appreciated that any other means of attaching and re-attaching, and the associated usage of corresponding calibration modes, should all be within the scope of the present disclosure.

What is claimed is:

1. An X-Ray Fluorescence (XRF) test system comprising an XRF test instrument used for testing a test target's responses to X-rays, the instrument including a test window allowing X-rays and its responsive energy to pass through, at least one window protecting film allowing the X-rays to pass through and provide protections to the window, wherein the film is configured to be coupled with the window in a fashion to be removable from or attached, or re-attached over the window, wherein the at least one film is configured to be removable and reattachably attached over the window by adhesive coupling along or partially along the circumference of the at least one film.

2. The system of claim 1 wherein the at least one film has a tensile modulus higher than 10,000 MPa, initial tear strength higher than 3 N, a low density of less than 2 g/cm$^3$ to allow transmission of X-rays and has a thickness of less than 100 μm.

3. The system of claim 1, wherein the at least one film includes a film made of polyimide material and having a thickness which is one of 25 μm and 75 μm.

4. The system of claim 1, wherein the test instrument further comprises an X-ray source, an X-ray detector, and a data analyzer.

5. The system of claim 4, wherein the data analyzer further comprises a calibration module including at least two calibration modes, of which the first mode corresponds to an operational status of the instrument without the protecting film being applied onto the window, the second mode corresponding to the operational status of the instrument with the protecting film applied onto the window.

6. The system of claim 5, wherein the first mode is configured for testing elements with lighter atomic numbers; the second mode is configured for testing elements with heavier atomic numbers.

7. The system of claim 5, wherein the second mode corresponds to calibration values obtained for different numbers and different kinds of the protecting film being attached to the window.

8. The system of claim 7, wherein calibration values for a specific one of the at least one film is obtained from calibration procedures on the XRF instrument with the specific one of the at least one film attached.

9. The system of claim 7, wherein calibration values for a specific one of the at least one film is calculated by applying a calibration value of the first mode with a corresponding calibration factor specific to the specific one of the at least one film.

10. The system of claim 9, wherein the calibration factor is obtained by comparing the calibration values obtained with and without the specific one of the at least one film applied.

11. The system of claim 5, wherein the calibration modes encompass the entire or any part of possibilities under which any and any number of the at least one protecting film is applied to the window.

12. The system of claim 5, wherein the first mode is configured for testing element Ti or other like elements; the second mode is configured for testing Mo or other like elements.

13. The system of claim 5, wherein the data analyzer is configured, during a calibration session, to execute the steps including:

checking the calibration mode that the instrument is set in in a previous test session and the film application;
prompting a user whether and how many of the at least one film is currently applied, and recommending which of the at least one film should be applied;
confirming which of the at least one, or none, of the film is being used for the present testing;
selecting the first or the second calibration mode according to the film applied;
calibrating and readying the instrument for testing.

14. The system of claim 13, wherein the steps further include identifying which kind and how many of the at least one film are applied.

15. The system of claim 14, wherein the steps further include providing checking and identifying whether the identified film is a good match to the test as tasked.

16. The system of claim 15, wherein the steps further include prompting an operator when the identified film application is not a good match with the test as tasked.

17. A method of providing at least one window protecting film allowing X-rays to pass through and providing protections to a test window of an XRF test instrument, the method including the steps of: providing the film with an adhesive coupling along or partially along the circumference of the film, attaching the at least one film over the window in a removably and reattachably attached manner via the adhesive coupling, wherein the XRF test instrument is used for testing a test target's responses to X-rays.

18. At least one window protecting film allowing X-rays to pass through and providing protections to a test window of an XRF test instrument, the film being applied with an adhesive coupling such that the film configured to be removably and reattachably attached to the window via the adhesive coupling along or partially along the circumference of the at least one film, and wherein the XRF test instrument is used for testing a test target's responses to X-rays.

* * * * *